US009844741B2

(12) United States Patent
Raedts (10) Patent No.: US 9,844,741 B2
(45) Date of Patent: Dec. 19, 2017

(54) DISPOSABLE HORIZONTAL OR RADIAL FLOW TYPE CHROMATOGRAPHIC COLUMN

(75) Inventor: Marcellus Johannes Hubertus Raedts, Emmen (NL)

(73) Assignee: JEMP HOLDING BV, Emmen (NL)

(*) Notice: Subject to any disclaimer, the term of this patent is extended or adjusted under 35 U.S.C. 154(b) by 238 days.

(21) Appl. No.: 13/994,290

(22) PCT Filed: Dec. 16, 2011

(86) PCT No.: PCT/NL2011/050858
§ 371 (c)(1),
(2), (4) Date: Jun. 14, 2013

(87) PCT Pub. No.: WO2012/081983
PCT Pub. Date: Jun. 21, 2012

(65) Prior Publication Data
US 2013/0270167 A1   Oct. 17, 2013

(30) Foreign Application Priority Data
Dec. 16, 2010  (NL) .................................. 2005873

(51) Int. Cl.
*B01D 15/18* (2006.01)
*B01D 15/22* (2006.01)
(Continued)

(52) U.S. Cl.
CPC ............ *B01D 15/18* (2013.01); *B01D 15/22* (2013.01); *G01N 30/38* (2013.01); *G01N 30/50* (2013.01);
(Continued)

(58) Field of Classification Search
CPC ............ G01N 2030/386; G01N 30/60; G01N 30/6004; G01N 30/6017; G01N 30/603;
(Continued)

(56) References Cited

U.S. PATENT DOCUMENTS 4,627,918 A    12/1986  Saxena
4,676,898 A *  6/1987   Saxena ..................... 210/198.2
(Continued)

FOREIGN PATENT DOCUMENTS

WO       2007/136247 A1    11/2007

OTHER PUBLICATIONS

Cabanne et al.: "Evaluation of radial chromatography versus axial chromatography, practical approach", Journal of Chromatography B: Biomedical Sciences & Applications, Elsevier, Amsterdam, NL, vol. 845, No. 2, Jan. 12, 2007 (Jan. 12, 2007), pp. 191-199, XP005865228, ISSN: 1570-0232, 001: 10.1016/J.JCHROMB.2006.07.064 figures 1,3A abstract.
(Continued)

*Primary Examiner* — Patrick Orme
(74) *Attorney, Agent, or Firm* — Young & Thompson (57) ABSTRACT

A liquid chromatography column, utilizing horizontal or radial flow of sample material passing there through, includes a housing defining a chamber therein, at least one removable screw lid, and first and second longitudinally extending porous frits positioned within the chamber. A bed or packing of particulate, chromatographic separation material is positioned within the chamber and intermediate the porous frits, the first of the porous frits being adjacent the housing and an inlet channel, the second of the porous frits being positioned adjacent a core member and an outlet channel. A distributor is operatively connected to the inlet channel, and a collector is connected to the outlet channel. The distributor and the inlet channel are constructed to direct associated material to be separated in the bed evenly across a longitudinal length of the bed in a horizontal direction.

8 Claims, 11 Drawing Sheets

(51) Int. Cl.
*G01N 30/38* (2006.01)
*G01N 30/50* (2006.01)
*G01N 30/60* (2006.01)

(52) U.S. Cl.
CPC ........... *G01N 30/60* (2013.01); *G01N 30/603* (2013.01); *G01N 30/6091* (2013.01); *G01N 30/6017* (2013.01); *G01N 2030/386* (2013.01)

(58) Field of Classification Search
CPC .... G01N 30/6091; B01D 15/14; B01D 15/18; B01D 15/22
See application file for complete search history.

(56) References Cited

U.S. PATENT DOCUMENTS

| 5,667,676 | A * | 9/1997 | Alaska | B01D 15/206 |
| | | | | 210/198.2 |
| 2008/0017579 | A1* | 1/2008 | Hermansson et al. | 210/656 |
| 2009/0120873 | A1* | 5/2009 | Becker | B01D 61/14 |
| | | | | 210/636 |

OTHER PUBLICATIONS

International Search Report, dated May 14, 2012, from corresponding PCT application.

* cited by examiner

DISPOSABLE HORIZONTAL OR RADIAL FLOW TYPE CHROMATOGRAPHIC COLUMN

BACKGROUND OF THE INVENTION

Field of the Invention

The present invention relates to a column for liquid chromatography, which includes a column tube intended to be filled with a separation medium, and inlet and outlet means.

Description of the Related Art

It is often necessary or desirable to fractionate a fluid mixture to separate out/isolate useful or desired components. This can be achieved by using liquid chromatography systems.

Chromatography systems of various sizes are used in both laboratory analysis operations and for industrial scale production operations in which separation steps such as fractionation from human blood or capturing or removing impurities from a pharmaceutical can be carried out on a large scale in a batch process.

Liquid chromatography may briefly be described as the fractionation of components of a mixture based on differences in the physical or chemical characteristics of the components. The various liquid chromatographic systems fractionate the components with a fractionation matrix. Some liquid chromatographic matrix systems fractionate the components of a mixture based upon such physical parameters as molecular weight. Still other liquid chromatographic systems will fractionate the components of a mixture based upon such chemical criteria as ionic charge, hydrophobicity, and the presence of certain chemical moieties such as antigenic determinants or lecithin-binding sites on the components.

Liquid chromatography often uses a separation column. The separation column contains a packing or matrix medium or material, as well known in the art, which interacts with the various components of the sample fluid to be separated. The composition of the separating medium depends on the fluid being directed there through so as to produce the desired separation.

In order to prepare a chromatographic column to be able to separate biological substances effectively, it is usual to pack fine particles of separation material as tightly and as uniformly as possible in the column tube. Filling of the column, or column packing as it is often referred to, is normally effected by closing one end of the column with an outlet means which includes a filter element, and pumping a liquid suspension of the particles under pressure into the other end of the column. Whereas the pumped liquid is able to pass through the filter element essentially unobstructed, the particles are retained by the filter element, so as to build up a particle bed along the length of the tube. As the column tube is filled, the particles are pressed out towards the wall of the tube and the particle bed obtains a stable compaction state with the particles well distributed, this state being maintained during the whole of the filling process.

The first type separation columns generally known in the art are of a cylindrical construction and the fluid flows axially through a separating medium bed (packing or matrix) retained in the column. The medium bed is retained between supports or frits on either or both ends of the column. As the sample and elution fluids pass through the separating medium bed, the constituents of the sample fluid travel at different rates due to their interaction with the matrix or packing material. As a result, these constituents emerge separated (i.e., have different elution times) in the outlet stream of the column.

With the need for high performance chromatography, horizontal or radial flow type chromatographic columns were developed. Such horizontal or radial flow columns are, e.g., described and claimed in U.S. Pat. Nos. 4,627,918 and 4,676,898. In the horizontal or radial flow type columns, the sample and elution fluids are introduced via a distributor to the outer periphery or circumferential wall or surface of the separating medium or matrix, which consists of packing material, where the components get separated and the fluids pass horizontally or radially inwardly through the separation medium to a central or collection port and then elute from the column at different times and at different rates. This horizontal flow column design has a high cross sectional area and very low effective bed height. It thus offers the ability to handle very high flow rates at low operative pressures.

As used herein, the terms "horizontal or radial flow mode", which are used interchangeably, are defined as flow of the sample or eluant fluid through the chromatographic column in a direction that is perpendicular to the longitudinal axis of the column, regardless of the position of the column relative to the work bench or support stands or other equipment used to support or stack the columns.

This chromatographic separation in a horizontal mode may be accomplished by means of a chromatographic column constructed so as to have an inner and outer annuli, with the matrix material being packed there between. The bed height is thus computed as the distance between the inner and outer annuli. Chromatography consequently takes place radially in the column. Furthermore, horizontal flow may also be achieved in a cubic arrangement where the flow takes place between two vertically held end plates.

This horizontal mode column configuration results in even bed height since the inlet and outlet distributors are fixed. The distributor and collection channels are designed to provide even application of the sample and horizontal streamlines across the chromatographic bed. The long, vertical column assembly with horizontal flow is easy to fabricate and convenient for packing and handling. Furthermore, since the bed height is constant along the length of the column, both the cross-sectional area and bed volume are proportional to the column length. Thus, scale-up is possible by linearly increasing the length of the column in proportion to the desired scale of operation. At any scale of operation, the pressure drop remains constant and scale up is accomplished easily by linear increments of the column bed length.

The horizontal mode column is particularly applicable to high performance chromatography used in conjunction with the separation of biomolecules or other organic or inorganic compounds. This column type is capable of use both in high performance and conventional chromatography, in the identification and separation of mixtures in the preparative mode, and also provides scale-up to larger columns for use in the isolation of components from mixtures in quantities suitable for industrial or production purposes.

The development of chromatography columns has aimed at providing ease of operation and various additional benefits which have particular commercial importance. These include: (a) the ability to be sterilized by autoclaving; (b) improved sanitation by virtue of design features giving less carryover of product from one batch to the next; (c) the ability to resist solvents; (d) material conformity to food grade FDA regulations; (e) an improved pressure tolerance; (f) lower cost; (g) the potential for full or partial automation; (h) the ability to provide disposable columns.

SUMMARY OF THE INVENTION

The present invention provides a horizontal flow high performance chromatography column which is an improvement over the prior art column of this type by substantially lowering fabrication costs, providing a small footprint and yielding high throughput.

The invention relates to a liquid chromatography column, utilizing horizontal or radial flow of sample material passing there through comprising: a housing defining a chamber therein and including at least one removable axial/longitudinal end section, preferably screw lid (such that preferably by turning/rotating the section itself it can be mounted/dismounted relative to the column); a first (outer) and second (inner) axially/longitudinally extending porous frits or membranes positioned within said chamber of said housing; a bed or packing of, preferably particulate, chromatographic separation material positioned within said chamber of said housing and intermediate said porous frits, the first of said porous frits being adjacent a housing wall and defining with said wall a cylindrical shaped ring type inlet channel, the second of said porous frits being positioned adjacent a core member and defining with said core member a cylindrical shaped outlet channel; distribution means operatively connected to said inlet channel; collector means operatively connected to said outlet channel; a supply channel operatively connected to the distribution means and an exhaust channel operatively connected to the collector means; said distribution means and said inlet channel being constructed to direct associated material to be separated in said bed evenly across an axial/longitudinal length of said bed in a substantially horizontal direction.

Further, said porous frits are coaxially positioned with respect to one another. Practically, said first porous frit having a larger cross-section than said second porous frit and said core member is centrally located in said housing chamber.

Preferably, one or more of the further features apply to the inventive column: one of the axial end sections, preferably the removable lid is penetrated by both the supply and exhaust channel; the exhaust channel is coaxial with the first or second frit; the supply channel is radially spaced from the housing centre and/or the exhaust channel; the housing has a substantially cylindrical wall; the first and second frit are part of a cartridge removably contained in the housing; preferably within the cartridge at the one axial end the first and second frit are connected by an end wall closing the space between the first and second frit at said axial end and possibly having a passage for the outlet channel or core member, and/or at the opposite axial end the outlet channel is closed by an end wall connected to the second frit; the exhaust channel extends substantially the complete height of the chamber; the supply channel extends at an angle of at least 10 degrees relative to the exhaust channel; the cartridge, in the operative position within the chamber, extends from the end section opposite the removable lid beyond the axially extending housing wall; the exhaust channel extends inside, preferably lengthwise of, the core member and/or debouches at the axial/longitudinal end of the core member within the chamber; the core member extends substantially the complete height of the chamber; the core member penetrates the lid; the core member projects from the lid; the lid has a circumferential flange or depending skirt bearing internal, preferably repeatedly disconnectable and connectable, mounting means, e.g. screw thread, engaging external, preferably repeatedly disconnectable and connectable, mounting means, e.g. screw thread, at the axially extending housing wall; the lid has a central bore penetrated by the core member; the central bore of the lid has a circumferential, axially extending flange tightly engaging a circumferential recess in the top face of the top end wall connecting the first and second frit for positive locating of the packing within the housing; the core member is a separate part preferably bearing external, preferably repeatedly disconnectable and connectable, mounting means, e.g. screw thread, preferably engaging internal, preferably repeatedly disconnectable and connectable, mounting means, e.g. screw thread, of the closure; the core member keeps with its axial/longitudinal end a gap with the end section preferably opposite the removable lid and/or tapers towards the end section preferably opposite the removable lid; the distribution means comprise a radially narrowing, preferably the core member circumventing distribution space, preferably between the end section, preferably lid, and the space containing the packing and the supply channel preferably connects to, more preferably debouches into, said distribution space; the cross sectional area of the outlet channel increases, preferably continuously, along the axial direction, preferably due to the taper of the core member; one of the end sections, preferably the one opposite the lid, contains a means, such as a closable fill port, to supply the space between the frits with packing material for column packing purposes, while the column is completely assembled (e.g., a fill system according to WO2007136247 (Raedts)); between the core member and at least one of the lid and the cartridge or the end wall connecting the first and second frit a seal is present; the device has a handy outer dimension in the order of one liter contents.

BRIEF DESCRIPTION OF THE DRAWING FIGURES

The accompanying drawings, which are incorporated and form a part of the specification, illustrate an embodiment of the invention and, together with the description, serve to explain the principles of the invention.

DETAILED DESCRIPTION OF THE INVENTION

The liquid chromatography column shown in FIG. 1-11 comprises: a housing defining a chamber therein and including a removable screw lid such that this lid can be mounted and dismounted by turning around the lid; a first (outer) and second (inner) porous frits or membranes; a bed or packing of particulate chromatographic separation material positioned intermediate said porous frits; an axially extending core. The axially extending cylindrical external housing wall, first and second frit and core are coaxial.

The first frit is adjacent the axially extending cylindrical external housing wall and defines with said wall a cylindrical shaped ring type inlet channel. The second frit is adjacent the core member and defines with said core member a cylindrical shaped ring type outlet channel.

The lid is penetrated by both a supply and exhaust channel. The exhaust channel is coaxial with the core and extends through the core to debouch just above the bottom end wall of the housing. The supply channel is radially spaced from the core and the exhaust channel. The exhaust channel extends substantially the complete height of the chamber. The supply channel extends at an angle of 15 degrees relative to the exhaust channel. This allows for optimised supply flow characteristics.

Figure 1:
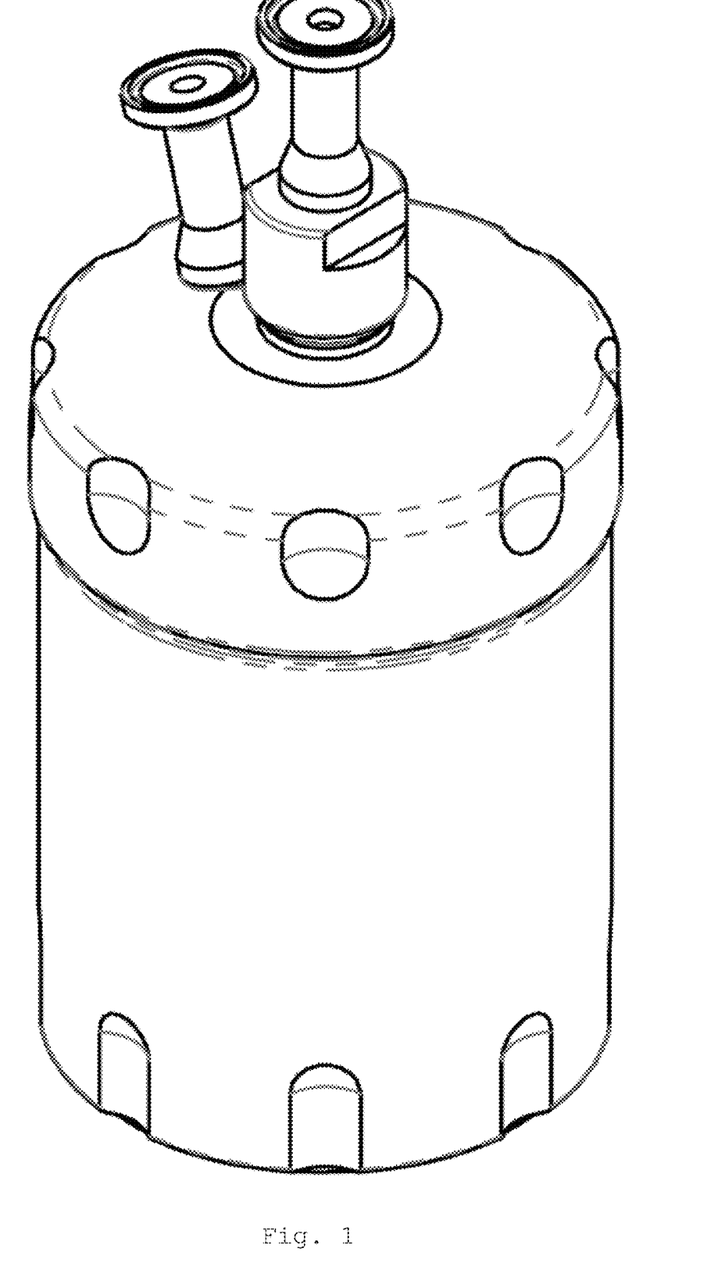
FIG. 1 shows the column in perspective view.
Figure 2:
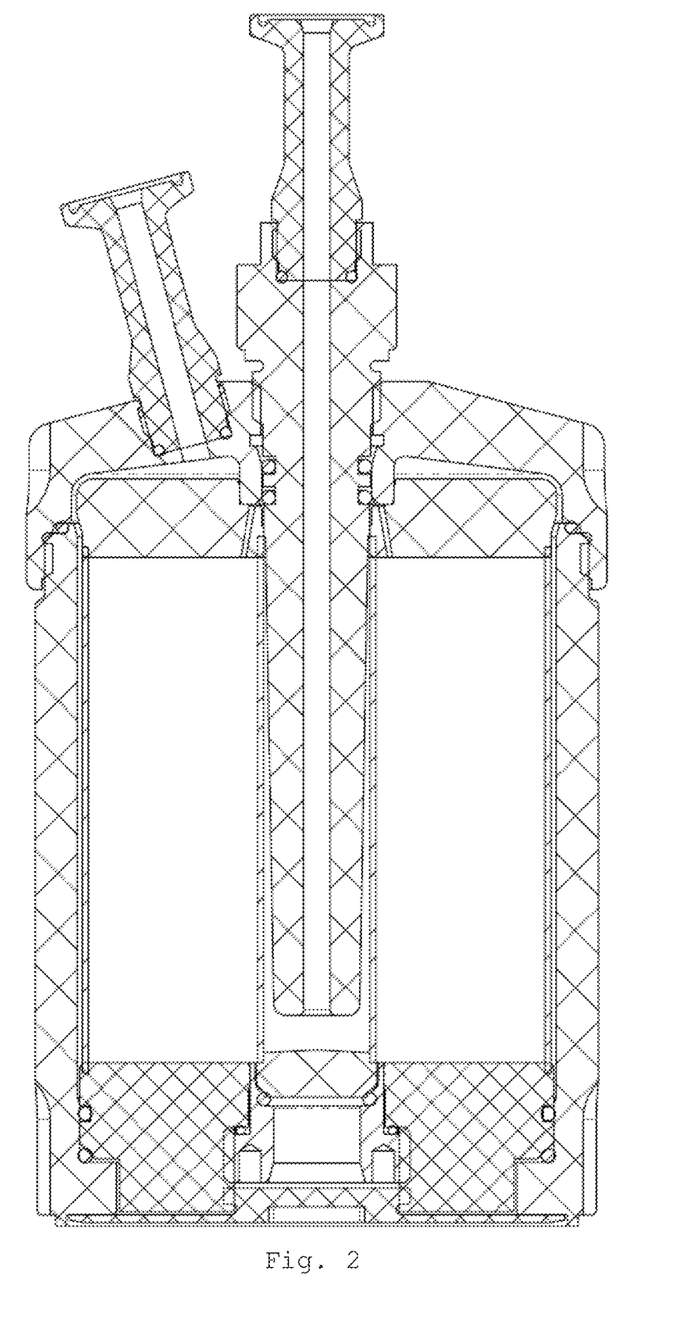
FIG. 2 shows the column of FIG. 1 in sectional side view.
Figure 3:
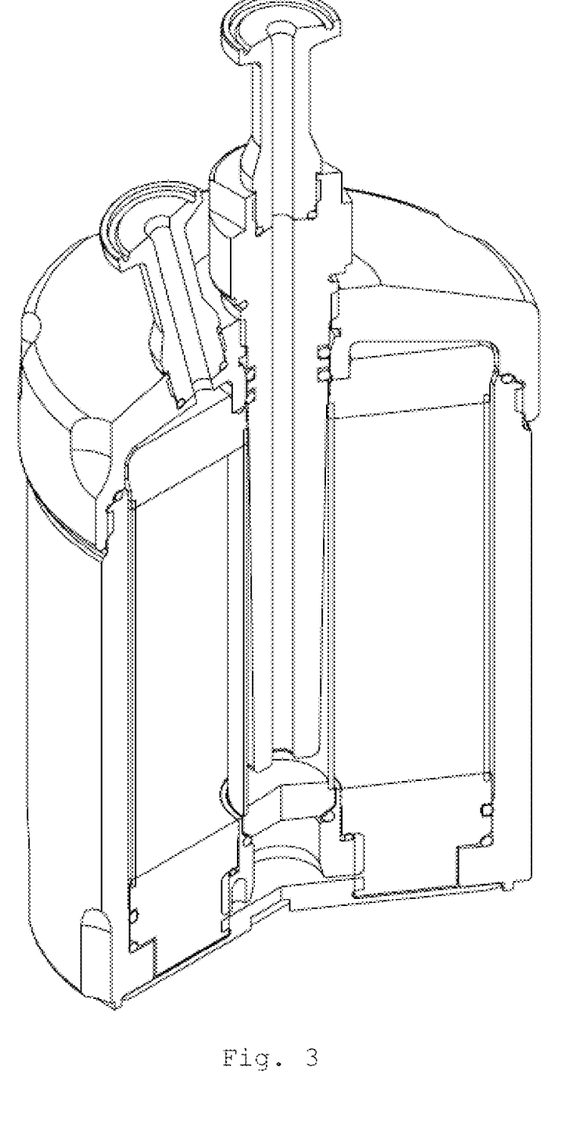
FIGS. 3 and 4 show the column of FIG. 1 in sectional perspective view from two different angles.
Figure 4:
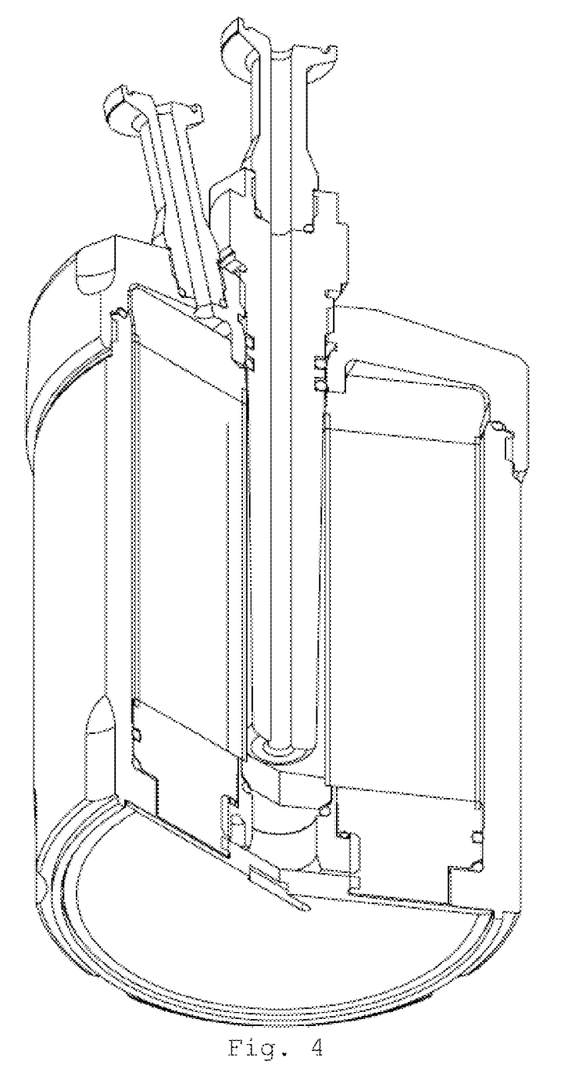
Figure 5:
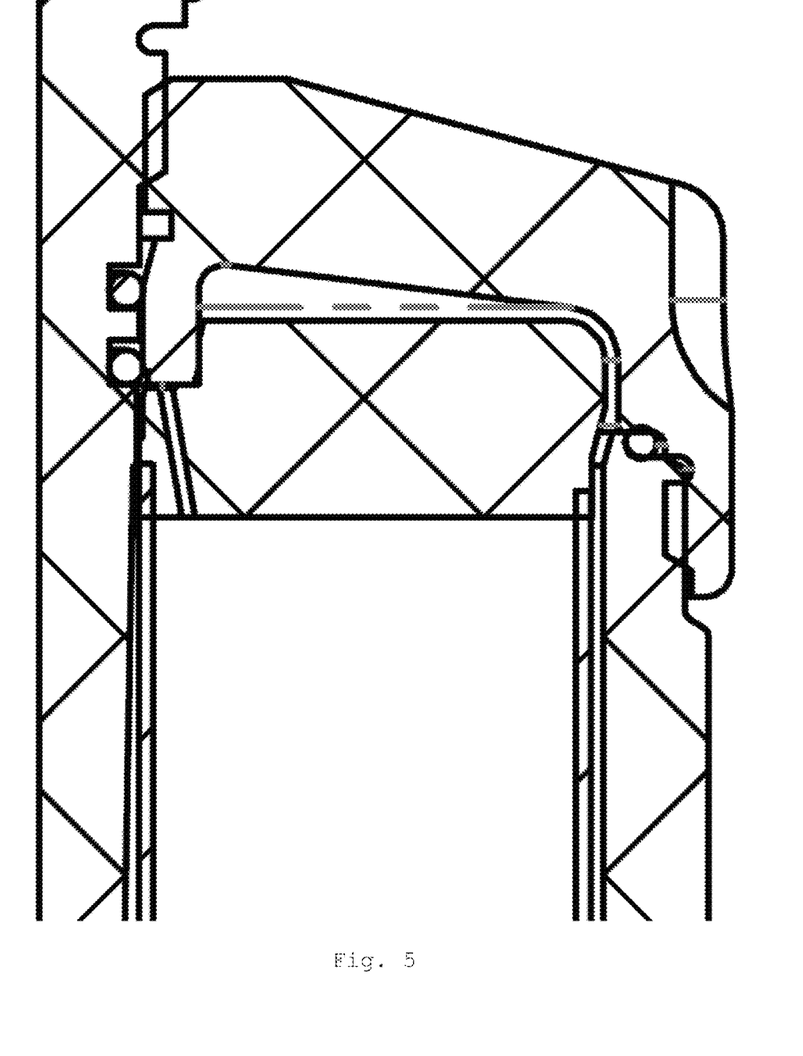
FIG. 5 shows a detail of FIG. 2 at larger scale.
Figure 6:
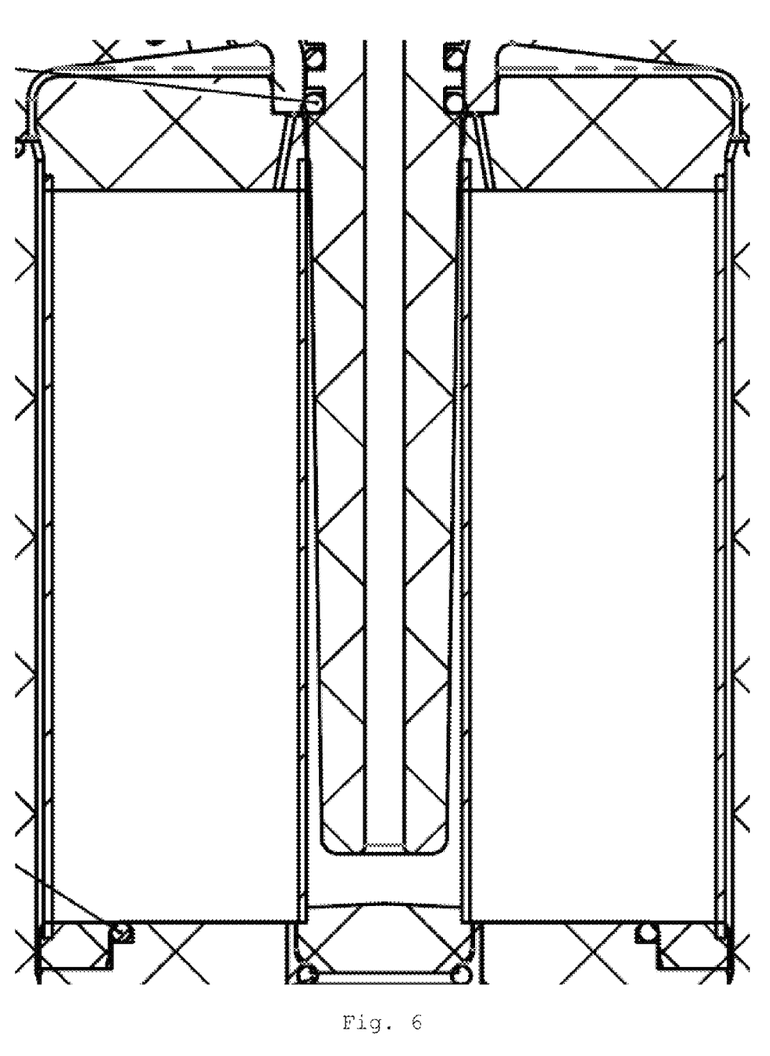
FIG. 6 shows a further detail of FIG. 2 at larger scale.
Figure 7:
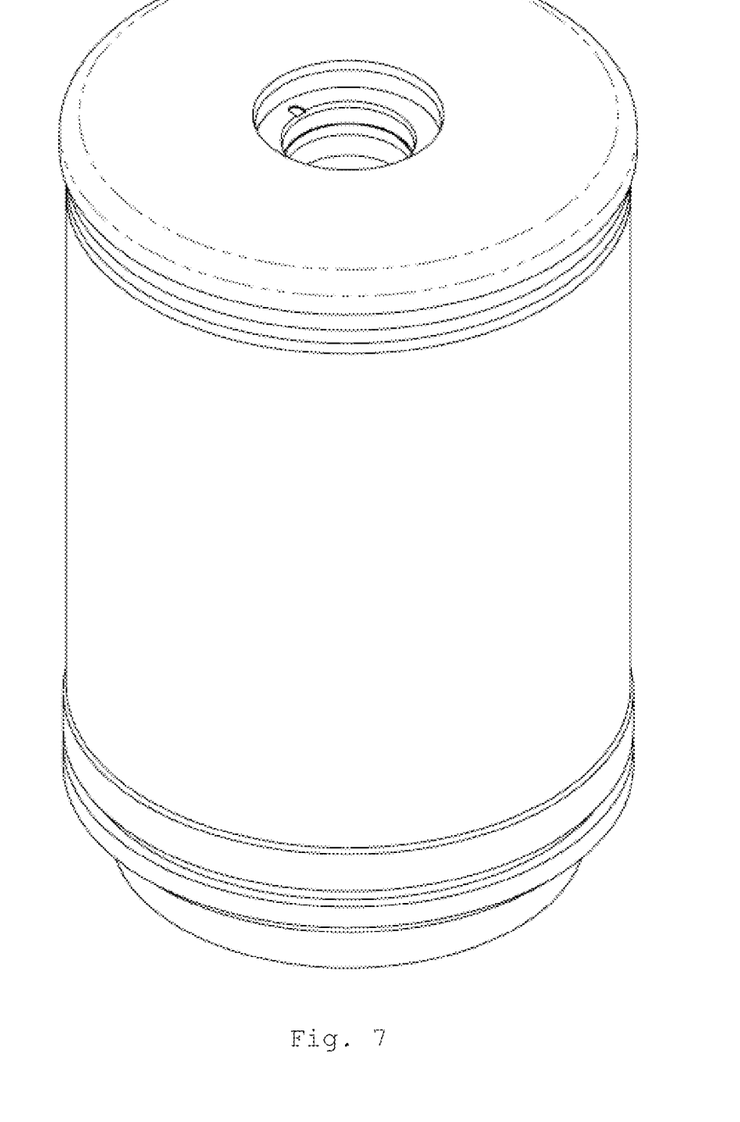
FIG. 7 shows a perspective view of the cartridge.
Figure 8:
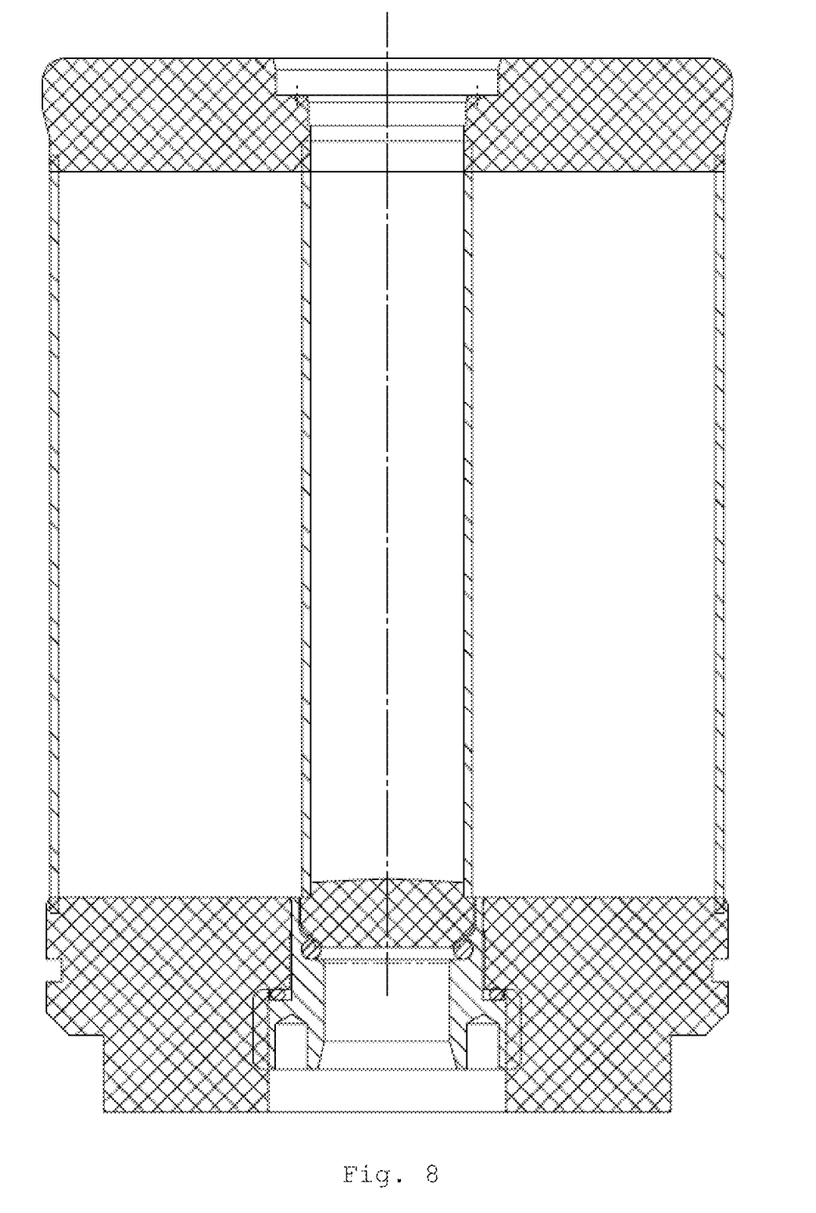
FIG. 8 shows the cartridge of FIG. 7 in sectional view.

The first and second frit are part of a cartridge removably contained in the housing. At both axial ends the first and second frit are connected by a radial extending end wall closing the space between the first and second frit to capture the doughnut shaped packing. The bottom end wall of the cartridge simultaneously provides the bottom wall of the housing and is releasable mounted to the axial housing wall through a circumferential shoulder at said wall.

The lid has a radially outer depending skirt bearing internal screw thread, engaging external screw thread at the axially extending housing wall. Viewed in the axial direction from the housing bottom end, the cartridge extends beyond the axially extending housing wall. The top part of the cartridge thus co extends with the depening skirt of the lid. This allows for ease of fine tuning of the merge of the distribution space and the inlet channel.

The cartridge plus the core almost completely fill the housing. Between the top face of the cartridge and the bottom face of the lid there is a distribution space into which the supply channel debouches. This distribution space tapers in the radial outward direction and merges at the radial outer circumference with the circumferential extending inlet channel. The circumferential outlet channel, surrounding the core, tapers towards the lid along the core and merges at the lower end of the core with a collector space delimited between the lower core end and the bottom end of the housing. This tapered shape of the outlet channel is due to the opposite taper of the core. The taper of the inlet and outlet channel optimises flow characteristics.

Figure 9:
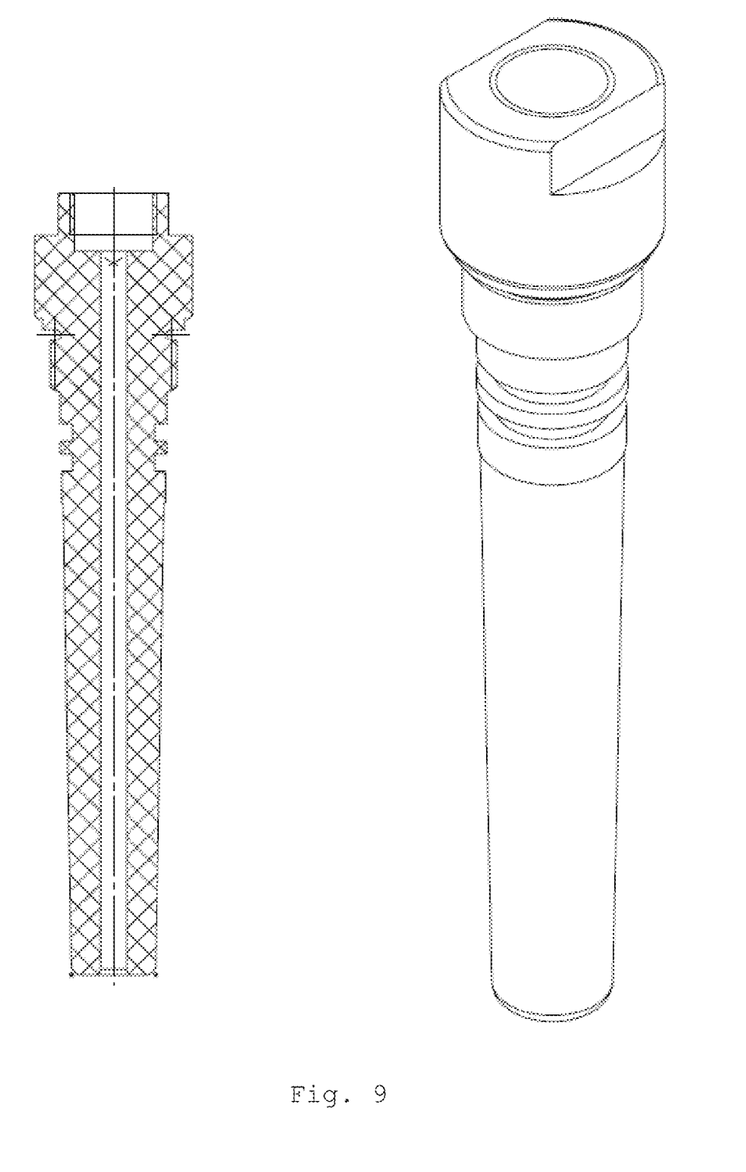
FIG. 9 shows the core member in sectional side view and in perspective view.
Figure 10:
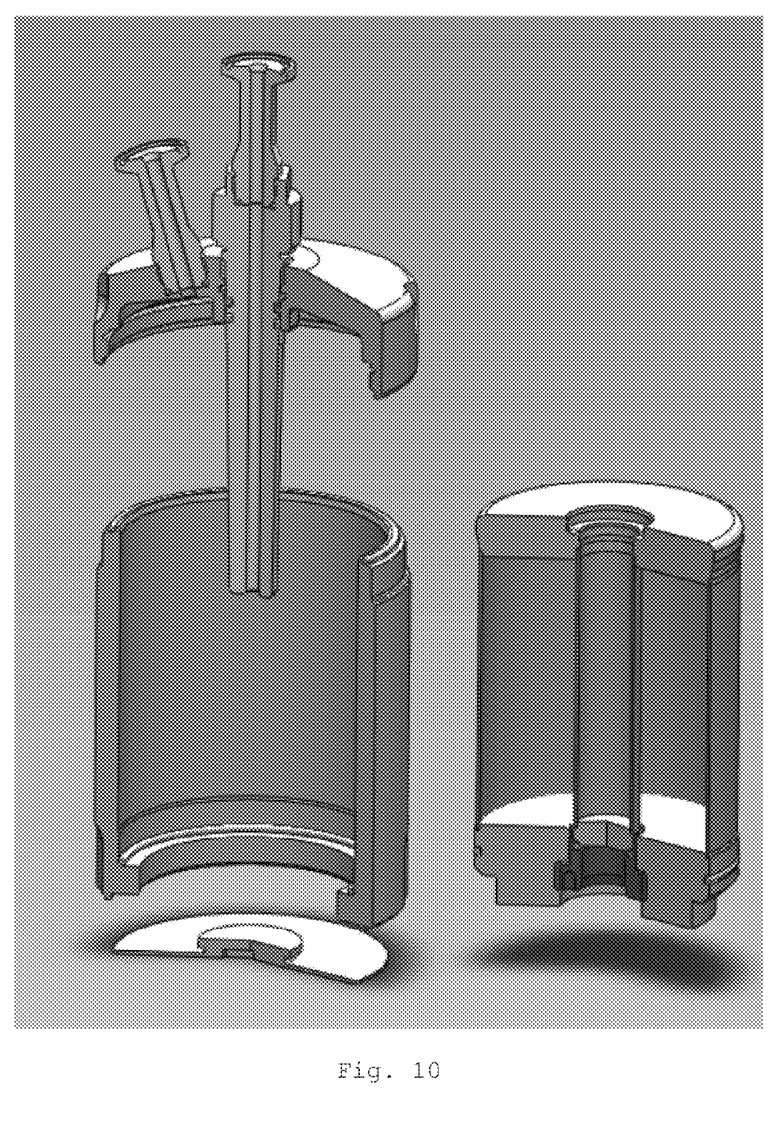
FIGS. 10 and 11 show the main elements in exploded view, the cartridge located aside the housing, wherein in FIG. 10 the main elements are shown in section.
Figure 11:
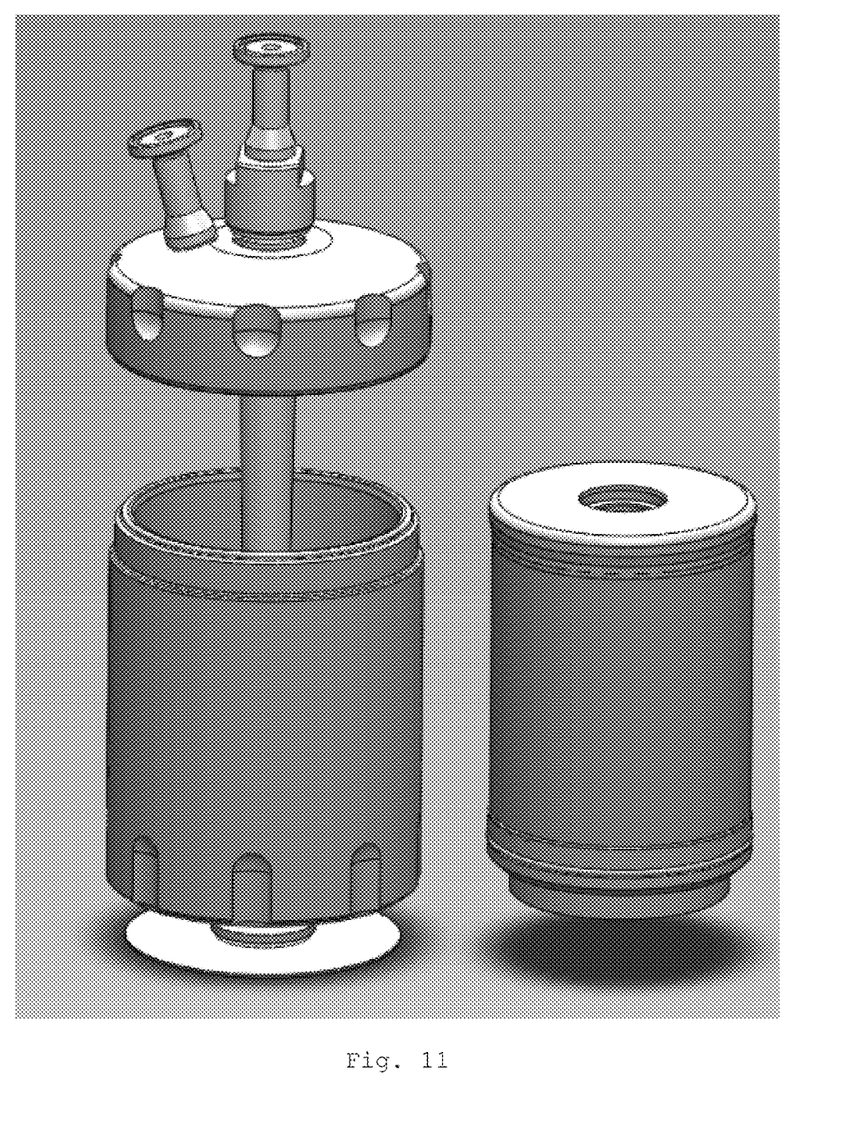

The core is a separate part bearing external screw thread engaging internal screw thread of a central bore in the lid. The central bore of the lid has a circumferential, axially extending flange or depending skirt tightly engaging a circumferential recess in the top face of the top end wall of the cartridge. Below the skirt, the core tightly penetrates the top wall of the cartridge. By means of this, both the lid and the core provide for positive locating of the cartridge within the housing. It could however be sufficient if only one of these positive locating means is applied.

The bottom end of the cartridge contains a centrally located closable fill port, to supply the space between the frits with packing material for column packing purposes.

O-ring type seals are applied to seal the core to the lid and the cartridge and to seal the lid to the axial extending housing wall.

The column operates as follows:

Fluid is introduced through the supply channel into the distribution space and from there flows radially outward towards the inlet channel. In the inlet channel the fluid flows axially downward to be evenly distributed across the complete surface of the first frit. Then, passing the first frit, the fluid flows radially inward through the packing to arrive at the second frit. Subsequently the fluid flows evenly distributed across the complete surface of the second frit through the second frit to arrive into the outlet channel. The fluid flows axially downward through the outlet channel, along the outer face of the core to be collected in the collection space. From there the fluid flows into the exhaust channel to flow axially upward through the core.

The cartridge can be replaced by unscrewing the lid and subsequently axially extracting the core from the cartridge while axially removing the lid. The cartridge is subsequently lifted from the inward projecting shoulder at the lower end of the circumferential wall of the housing by axially extracting the cartridge. Extracting/removing the lid, core and cartridge takes place in the same direction.

Further embodiments are also covered by the attached claims. E.g. the flow direction of the introduced fluid can be opposite, for which the supply, exhaust, inlet and outlet elements are interchanged.

The invention claimed is:

1. A liquid chromatography column, utilizing radial flow of sample material passing there through in an inward direction, comprising:
    a sealed housing defining a chamber therein;
    longitudinal closing opposite end sections of the sealed housing of which one end section is removable and provided by a screw lid, the screw lid having a radially outer depending skirt bearing an internal screw thread;
    a cylindrical housing wall longitudinally extending between and connecting to said opposite end sections and closing the housing, the cylindrical housing wall bearing an external screw thread that engages the internal screw thread of the screw lid;
    a first and a second longitudinally extending, cylindrical porous frit positioned within said chamber of said sealed housing;
    a doughnut shaped packing of particulate chromatographic separation material contained in a longitudinally sealed doughnut shaped packing space positioned within said chamber and intermediate said first and second porous frits, the first porous frit being adjacent said cylindrical housing wall and a sample material inlet channel of the housing, the second porous frit being positioned adjacent from said screw lid towards the opposite end section furthest from the screw lid;
    a longitudinally extending tapered core member, the tapered core member tapering towards an end section opposite the screw lid, such that a cross sectional area of a longitudinal centrally located outlet channel of the housing increases continuously in an axial direction, the tapered core member being mounted in a separate, self-contained partially penetrating through hole in the screw lid and such that the tapered core member partly projects outside the housing at a side of the screw lid, the tapered core member being a separate part bearing an external screw thread engaging an internal screw thread of a central bore in the screw lid;
    first and second o-rings sealing the core to the screw lid, the first and second o-rings being below the external screw thread engaging the internal screw thread of the central bore in the screw lid;
    a third o-ring sealing the screw lid to the longitudinally extending housing wall, the third o-ring being above the internal screw thread of the radially outer depending skirt of the screw lid;
    both the sample material inlet and outlet channels extend from outside the housing through said screw lid into the housing, the inlet channel extending straight externally from the housing, and externally from the housing the inlet channel is radially outwardly spaced from a longitudinal housing centre and extends at an angle of at least 10 degrees relative to the longitudinal housing centre;

said porous frits are coaxially positioned with respect to one another and with respect to said tapered core member, said first porous frit having a larger cross-section than said second porous frit, and said tapered core member is centrally located in said housing chamber;

a length of the tapered core member containing a longitudinally extending outflow channel connecting to said outlet channel, and the tapered core member covers a distance between the opposite end sections and keeps at a longitudinal end of the tapered core member a gap with the end section opposite the removable screw lid, and the outlet channel provides a straight extension of the outflow channel and extends externally from the housing such that a complete length of the tapered core member contains a channel provided by the outlet channel and the outflow channel;

within the housing is a distribution space into which said inlet channel debouches, the distribution space tapering in a radial outward direction and merges at a radial outward circumference with the inlet channel;

a collector space within the housing is operatively connected to said outlet channel, the collector space being delimited between a lower end of the tapered core member and a bottom end of the housing;

said distribution space and said inlet channel being constructed to direct associated sample material, supplied to the housing to be separated in said packing of separation material evenly across a longitudinal length of said packing of separation material;

said collector space and said outlet channel being constructed to remove associated sample material processed in said packing of separation material evenly across a longitudinal length of said packing of separation material, such that during operation of the apparatus said sample material enters the housing through the inlet channel and then flows further to become evenly distributed across the first frit and then flows in a substantially radial direction inwards through said doughnut shaped packing of separation material and then exits the packing space evenly distributed through the second frit and is subsequently collected by said outflow channel and then flows through the outlet channel to exit the housing;

wherein the packing of separation material is contained in a removable, self-contained cartridge providing said packing space, said cartridge comprising the first and the second frit, a first longitudinal end wall, penetrated by the tapered core member, and a spaced, opposite second longitudinal end wall, said first and second longitudinal end walls connecting both frits and longitudinally sealing the packing space, which cartridge is separate from the screw lid and the cylindrical housing wall, such that the cartridge can be removed from the housing as a self-contained unit by removing the screw lid, the cartridge is positively located radially at the first longitudinal end wall of the cartridge by the radially outer depending skirt of the screw lid in that said skirt abuts and is fitted to said first longitudinal end wall of the cartridge, the central bore of the screw lid having the skirt circumferentially extending around the central bore, and the cartridge is located longitudinally by and is fitted between the lid and an inward projection of and unitary with the cylindrical housing wall at the level of the second longitudinal end wall, the design being such that the cartridge can be replaced by unscrewing the screw lid from the housing and subsequently axially extracting the tapered core member from the cartridge while axially removing the screw lid from the housing and subsequently the cartridge is lifted from the inward projection at the level of the second longitudinal end wall by axially extracting the cartridge from the housing, wherein the screw lid, tapered core member and cartridge move in the same direction relative to the housing, and wherein after passing the second frit the sample material collects at the lower end of the tapered core member and from there enters said lower end of the tapered core member and flows longitudinally through the tapered core member to exit the liquid chromatography column.

2. The liquid chromatography column according to claim 1, wherein the tapered core member has a radial ridge engaging a radial ridge at the screw lid retaining the core member penetrating into the housing.

3. The liquid chromatography column according to claim 1, wherein the cartridge is located radially, at the first longitudinal end wall of the cartridge, adjacent the screw lid, by the tapered core member in that said tapered core member, from the side of the screw lid, penetrates and is fitted to said first longitudinal end wall of the cartridge.

4. The liquid chromatography column according to claim 1, wherein the cartridge is located radially at a second longitudinal end wall of the cartridge by and is fitted with the cylindrical housing wall surrounding the second longitudinal end wall.

5. The liquid chromatography column according to claim 1, wherein the outlet channel tapers towards the screw lid such that by rotating the screw lid itself can be mounted/dismounted relative to the column.

6. The liquid chromatography column according to claim 1, the first of said porous frits being adjacent a housing wall and defining with said wall a cylindrical shaped ring inlet channel, the second of said porous frits being positioned adjacent the tapered core member and defining with said tapered core member a cylindrical shape of the outlet channel, such that in the inlet channel the fluid flows axially downward to be evenly distributed across a complete surface of the first frit and the fluid flows evenly distributed across a complete surface of the second frit through the second frit to arrive into the outlet channel.

7. The liquid chromatography column according to claim 1, wherein the inlet channel extends at an angle of 15 degrees relative to the longitudinal housing centre.

8. A liquid chromatography column, utilizing radial flow of sample material passing there through in an inward direction, comprising:

a sealed housing defining a chamber therein;

longitudinal closing opposite end sections of the sealed housing of which one end section is removable and provided by a screw lid, the screw lid having a radially outer depending skirt bearing an internal screw thread;

a cylindrical housing wall longitudinally extending between and connecting to said opposite end sections and closing the housing, the housing wall bearing an external screw thread that engages the internal screw thread of the screw lid;

a first and a second longitudinally extending, cylindrical porous frit positioned within said chamber of said sealed housing;

a doughnut shaped sealed packing of particulate chromatographic separation material positioned within said chamber and intermediate said first and second porous frits, the first porous frit being adjacent said cylindrical housing wall and a sample material inlet channel of the housing, the second porous frit being positioned adjacent from said screw lid towards the opposite end section furthest from the screw lid;

a longitudinally extending tapered core member, the tapered core member tapering towards the end section opposite the screw lid, such that a cross sectional area of a longitudinal centrally located outlet channel of the housing increases continuously in an axial direction, the tapered core member being mounted in a separate, self-contained partially penetrating through hole in the screw lid and such that the tapered core member partly projects outside the housing at a side of the screw lid, the tapered core member being a separate part bearing an external screw thread engaging an internal screw thread of a central bore in the screw lid;

first and second o-rings sealing the core to the screw lid, the first and second o-rings being below the external screw thread engaging the internal screw thread of the central bore in the screw lid;

a third o-ring sealing the screw lid to the longitudinally extending housing wall, the third o-ring being above the internal screw thread of the radially outer depending skirt of the screw lid;

both the sample material inlet and outlet channels extend from outside the housing through said screw lid into the housing, the inlet channel extending straight externally from the housing, and externally from the housing the inlet channel is radially outwardly spaced from a longitudinal housing centre and extends at an angle of at least 10 degrees relative to the longitudinal housing centre;

said porous frits are coaxially positioned with respect to one another and with respect to said tapered core member, said first porous frit having a larger cross-section than said second porous frit, and said tapered core member is centrally located in said housing chamber;

the tapered core member containing a longitudinally extending outflow channel, and the tapered core member covers a distance between the opposite end sections and keeps at a longitudinal end of the tapered core member a gap with the end section opposite the removable screw lid, and the outlet channel provides a straight extension of the outflow channel and extends externally from the housing;

within the housing is a distribution space into which said inlet channel debouches, the distribution space tapering in a radial outward direction and merges at a radial outward circumference with the inlet channel; and a collector space within the housing is operatively connected to said outlet channel, the collector space being delimited between a lower end of the tapered core member and a bottom end of the housing;

wherein the packing of separation material is contained in a removable, self-contained cartridge providing said packing space, said cartridge comprising the first and the second frit, a first longitudinal end wall, penetrated by the tapered core member, and a spaced, opposite second longitudinal end wall, said first and second longitudinal end walls connecting both frits and longitudinally sealing the packing space, the self-contained cartridge is positively located radially at the first longitudinal end wall of the cartridge by the radially outer depending skirt of the screw lid in that said radially outer depending skirt abuts and is fitted to said first longitudinal end wall of the cartridge, the cartridge is located longitudinally by and is fitted between the lid and an inward projection of and unitary with the cylindrical housing wall at the level of the second longitudinal end wall, the design being such that the cartridge can be replaced, and wherein after passing the second frit the sample material collects at the lower end of the tapered core member and from there enters said lower end of the tapered core member and flows longitudinally through the tapered core member to exit the liquid chromatography column.

* * * * *